US00PP09775P

United States Patent [19]

Barnes et al.

[11] Patent Number: Plant 9,775

[45] Date of Patent: Dec. 31, 1996

[54] AGLAONEMA PLANT NAMED DEBORAH

[75] Inventors: J. Glenn Barnes, Apopka; Marcus S. Lambert, Zolfo Springs, both of Fla.

[73] Assignee: Sunshine Foliage World, Zolfo Springs, Fla.

[21] Appl. No.: 523,490

[22] Filed: Sep. 1, 1995

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 6,842 9/1995 Brown ..... Plt./88.1

*Primary Examiner*—James R. Feyrer

*Attorney, Agent, or Firm*—Foley & Lardner

[57] ABSTRACT

A new and distinct cultivar of Aglaonema named Deborah, characterized by its compact growth habit, its four-color patterned leaves with particularly showy white and yellow-green markings on both upper and lower surfaces, and white petioles and stems.

4 Drawing Sheets

The present invention comprises a new and distinct cultivar of Aglaonema, botanically known as *Aglaonema hybrid,* and referred to by the cultivar name Deborah.

The new cultivar is a mutation discovered by inventor, J. Glenn Barnes, in Apopka, Fla. in September 1993 among a tissue culture derived population of Aglaonema Queen of Siam, disclosed in U.S. Plant Pat. No. 6,842.

Asexual propagation by cuttings performed by inventor, J. Glenn Barnes at Apopka, Fla. and by inventor Marcus S. Lambert at Zolfo Springs, Fla. was used to increase the number of plants for evaluation and has demonstrated the stability of the combination of characterisitcs of the new cultivar from generation to generation.

The following observations, measurements and values describe plants grown in Zolfo Springs, Fla. under shade-house conditions which closely approximate those generally used in horticultural practice.

The following traits have been repeatedly observed to be characteristics which in combination distinguish Deborah from the parent cultivar Queen of Siam.

1. The color pattern on the upper leaf surface of Deborah is similar to that of Queen of Siam in that it has four colors on the upper surface. However, unlike Queen of Siam, the leaves of Deborah have white midribs and primary veins, and light yellow-green spots mottling the entire leaf surface.

2. The lower leaf surface of Deborah is abundantly marked with white spots and blotches. The midrib of the lower leaf surface is entirely white. By comparison, lower leaf surfaces of Queen of Siam have few white spots, and have green markings on the midrib.

3. The petioles of Deborah are entirely white, compared to the green and white marbled petioles of Queen of Siam.

4. The stems of Deborah are white, unlike Queen of Siam which has dark green stems spotted with white. 5. The leaves of Deborah are somewhat smaller than those of Queen of Siam.

All color references are measured against The Royal Horticultural Society Colour Chart. Colors are approximate as color depends to some degree on horticultural practices such as light level and fertilization rate, among others, without, however any variance in genotype.

The photographic drawings comprise color photographs and color photocopies, with the photo on Sheet 1 being a top perspective view of Deborah, the photo on Sheet 2 being a top perspective view of Queen of Siam, the photocopy on Sheet 3 showing the details of the color pattern on the upper and lower sides of a mature leaf of Deborah, and the photocopy on Sheet 4 showing the details of the color pattern on the upper and lower side of a mature leaf of Queen of Siam.

The photograph on Sheet 1 is of a plant of Deborah in a 26 cm pot approximately 18 months after planting a single 4 leaf cutting and grown under appropriate growing conditions. Colors are as accurate as possible with color illustrations of this type.

Classification: Aglaonema hybrid, cv, Deborah.

*Origin.*—Mutation discovered among a tissue culture derived population of Queen of Siam.

*Propagation.*—Asexual propagation either by division or tissue culture.

PLANT DESCRIPTION

Form: When a 4 leaf cutting is grown in a 26 cm pot for 18 months under appropriate growing conditions, Deborah is approximately 28 cm to 32 cm in height from the soil surface to the junction of the petioles of the last two (2) unrolled leaves, and approximately 80 cm to 88 cm in width.

Stem:

*Growth pattern.*—The stem is upright in growth and is approximately 2.0 cm to 2.3 cm in diameter five (5) cm above the soil surface. Internode distance is approximately 1.6 cm to 2.2 cm three (3) cm above the soil.

*Color.*—157 CD.

Petiole: The following information is based on the 4th expanded leaf from the apex.

*Growth pattern.*—The petiole wings (fleshy edges extending from the midrib) are approximately 1.1 mm to 1.3 cm wide one-half (½) the distance from the petiole base to the wing apex. The wings extend from the base of the petiole to within approximately 3.3 cm to 4.1 cm of the base of the leaf. The apex of the wings is acutely tapered, becoming flush with the petiole. The petiole follows the stem axis but diverges from the axis approximately 14 cm to 16 cm from the leaf base, forming a horizontal distance from the vertical axis to the leaf base of approximately 8.0 cm to 8.9 cm.

*Dimensions.*—The petiole is straight from its base to the tip of the wings, and often curved between the tip of the wings and the base of the leaf. The petiole is approximately 6 mm to 8 mm in diameter one-half (½) the distance between the top of the wing and the base of the leaf. The petiole is approximately 19 cm to 22.7 cm in length.

*Color.*—The petiole wings and the petiole midrib are 155 A.

Leaf:

*Growth pattern.*—The leaf is elliptic with a cuspidate apex and an obtuse base. The margin is entire. The leaf is asymmetric, with the side of the leaf unrolling first having less surface area than the side unrolling last. The leaf is oriented parallel to the stem axis at the time of full unrolling, changing to approximately 50 degrees from the stem axis as more leaves unroll above it. The midrib is straight, or curved upward slightly. The leaf blade is flat or somewhat wavy from the midrib to the margin.

*Dimensions.*—For the pot size and growing time indicated, the largest leaves are approximately 29 cm to 31 cm long and approximately 11.4 cm to 12.2 cm wide. Average sized leaves are approximately 25 cm to 29 cm long and approximately 8.9 cm to 10 cm wide. The leaf is moderately thick.

*Midrib.*—The midrib is thick and prominent, recessed on the upper leaf surface and protruding from the lower surface.

*Primary veins.*—The primary veins are sunken into the upper surface and protrude slightly from the underside. The primary veins are the same color as the tissue surrounding them. The leaf blade is slightly convex between the primary veins.

*Pattern.*—The central area of the upper leaf surface is 50% to 70% grey green. The margins of the leaf are dark green. Medium gray green blotches and spots follow the veins, and are most apparent in the dark green leaf margin. Yellow-green spots and blotches mottle the entire upper leaf surface. The lower leaf surface is abundantly marked with white spots and blotches, often covering approximately 50% to 85% of the surface area.

*Colors.*—Mature leaf — Upper surface: Grey-green central area, 191 B-C; margins are darker and greener than, but closest to, 137 A; green spots and blotches are 191 A; yellow-green spots are 145 A, 146 C, and the midrib and primary veins are 155 A. Mature leaf — Lower surface: 137 B, spotted with 155 A; midrib is 155 A. Newly opened leaf — Upper surface: Grey-green central area is 191 C-D; margins are darker and greener than, but closest to, 144 A; medium grey-green spots are greener than, but closest to, 191 A; yellow-green spots are 145 B-C, 150 D; midrib is 155 A, 150 D. Newly opened leaf — Lower surface: Greener than, but closest to, 146 C, spotted with 150 D; midrib is 155 A, 150 D.

*Axillary breaks.*—There are approximately 8 axillary breaks with at least one leaf expanded. Leaves will show true color and pattern by the first leaf.

Inflorescence: Typical of Aglaonema and does not have commercial significance.

Roots: Thick white roots with fine laterals.

General observations: Deborah is a compact growing variety having four-color leaves like its parent cultivar Queen of Siam. Deborah, however, has unusually abundant white and yellow green markings on the midribs, and leaf blades. Plants of Deborah are particularly showy, having colorful markings on both sides of the leaves. The petioles and stems are white, unlike those of Queen of Siam which are green and white marbled. These combined characteristics make Deborah a unique new cultivar.

I claim:

1. A new and distinct cultivar of Aglaonema plant named Deborah, as illustrated and described.

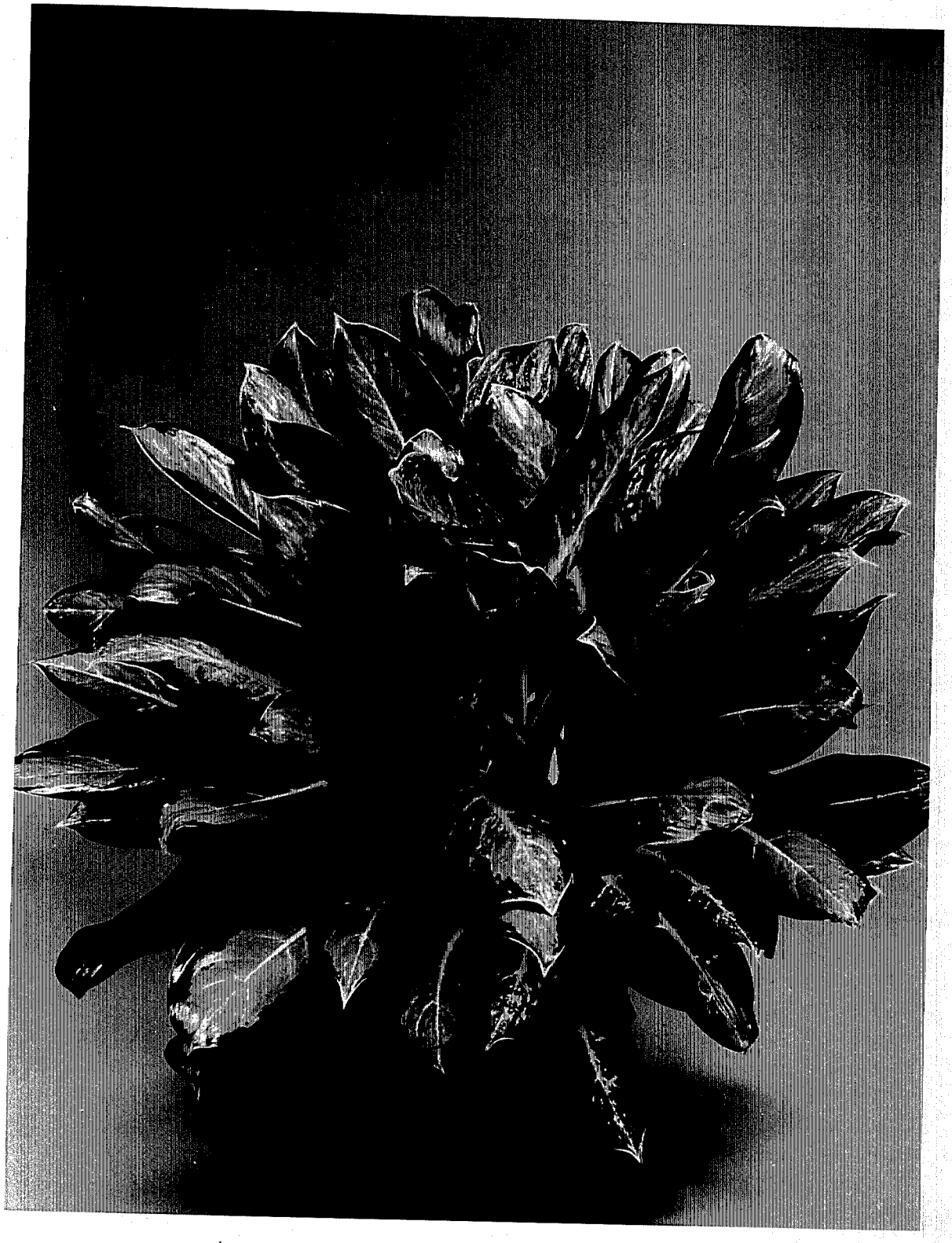

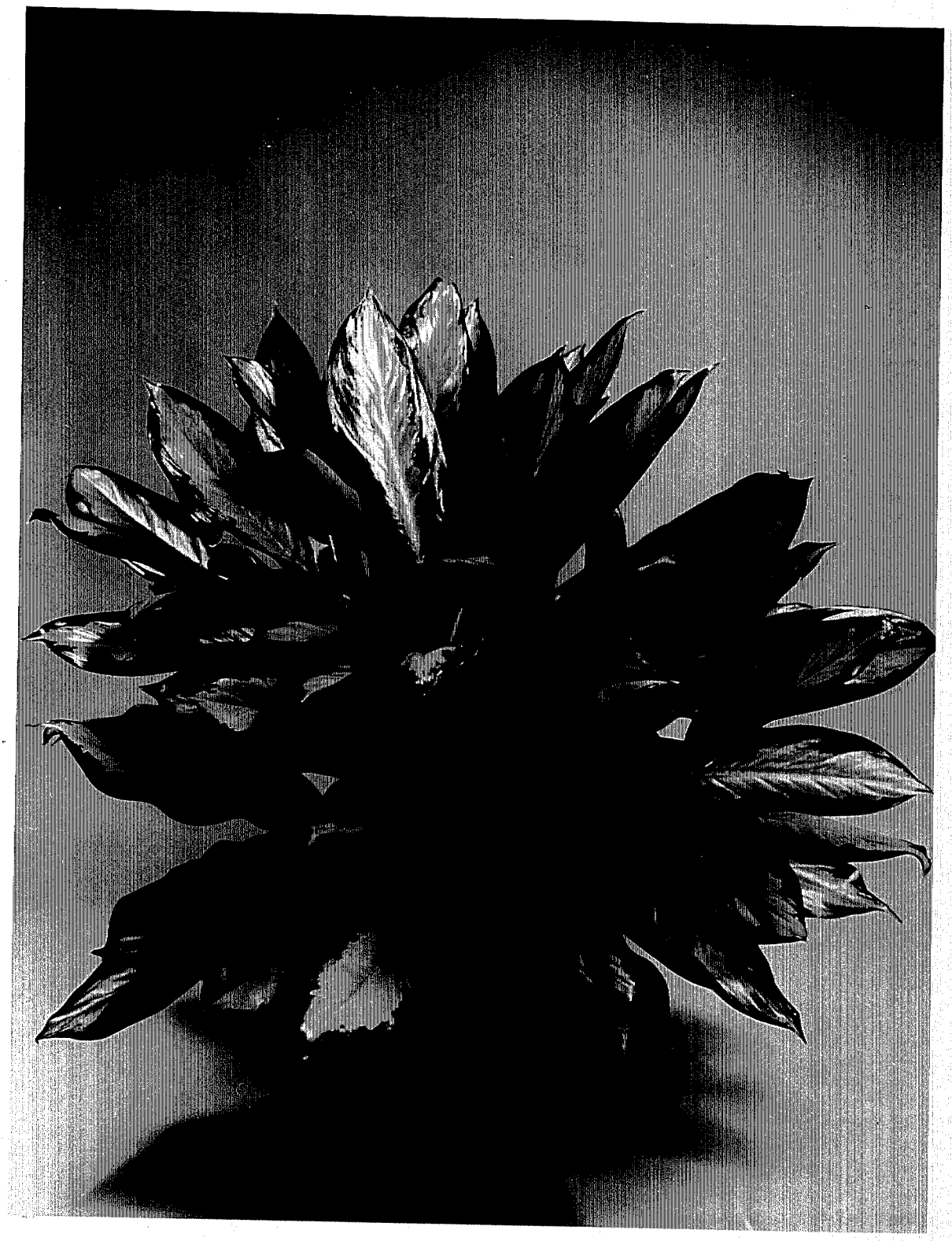

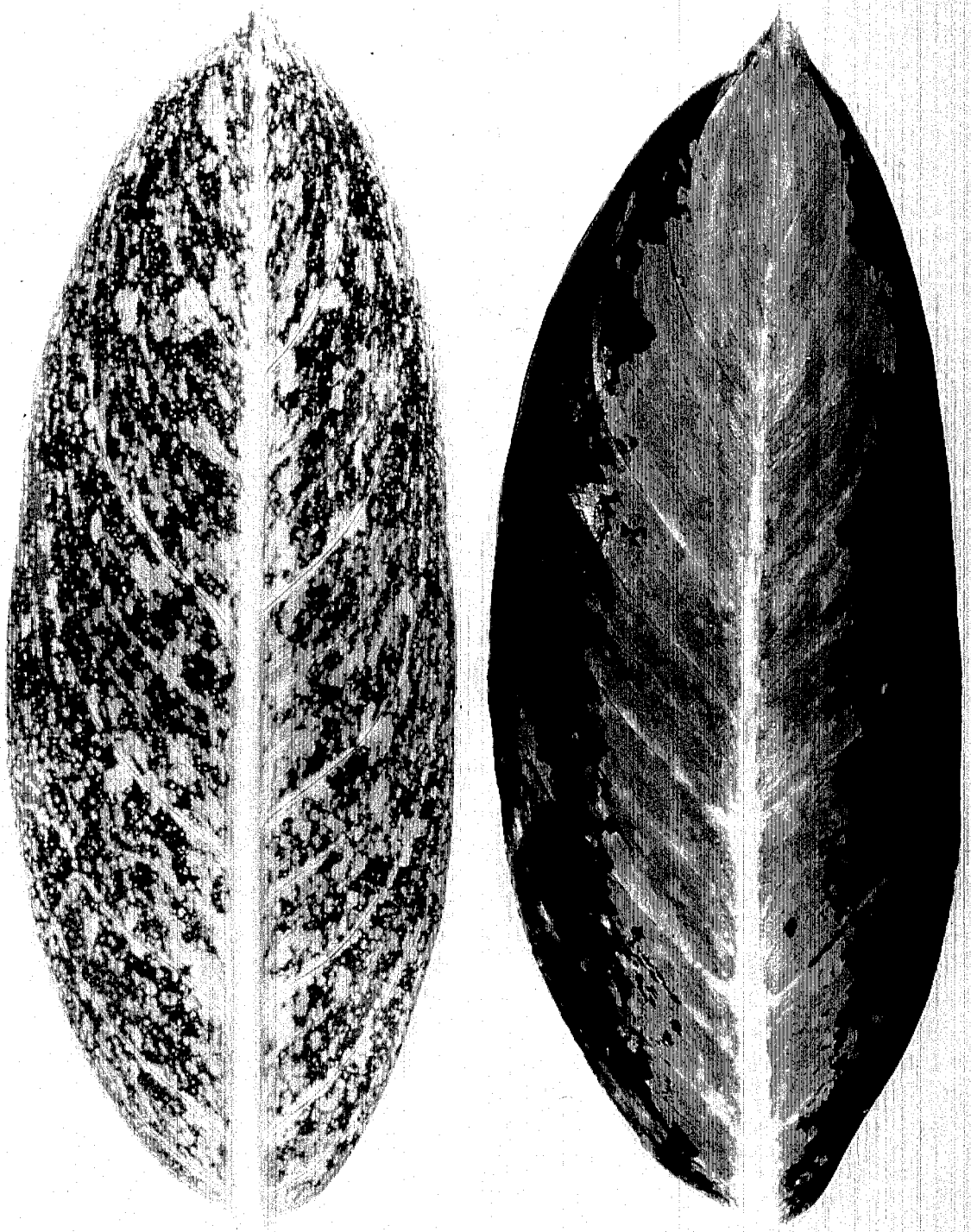

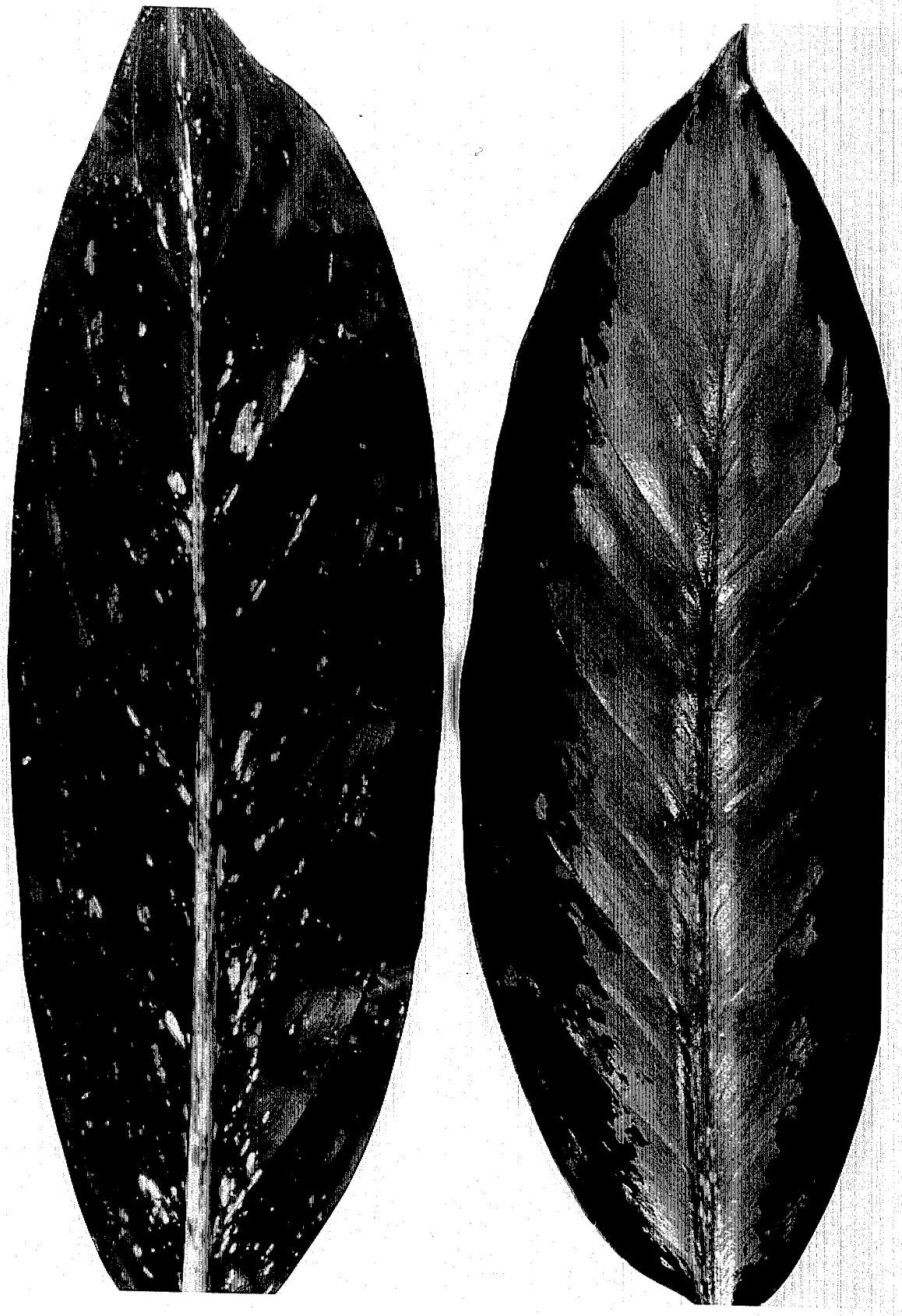

* * * * *